United States Patent [19] [11] 3,975,426
Yankee [45] Aug. 17, 1976

[54] 8β, 11β, 12α-PGF$_{2β}$ -COMPOUNDS
[75] Inventor: Ernest W. Yankee, Portage, Mich.
[73] Assignee: The Upjohn Company, Kalamazoo, Mich.
[22] Filed: Oct. 29, 1974
[21] Appl. No.: 518,430

Related U.S. Application Data
[60] Division of Ser. No. 374,405, June 28, 1973, which is a continuation-in-part of Ser. No. 289,317, Sept. 15, 1972, abandoned.

[52] U.S. Cl. .................. 260/468 D; 260/240 R; 260/247.2 R; 260/268 R; 260/293.65; 260/326.2; 260/343.3 R; 260/348 A; 260/345.2; 260/346.2 R; 260/429.9; 260/439 R; 260/448 R; 260/448.8 R; 260/469; 260/473 A; 260/476 R; 260/488 R; 260/488 CD; 260/501.1; 260/501.15; 260/501.17; 260/501.2; 260/514 D; 260/514 K; 260/520 B; 424/305; 424/308; 424/317
[51] Int. Cl.² ........................................ C07C 177/00
[58] Field of Search ...... 260/468 D, 514 D, 514 CA

[56] References Cited
UNITED STATES PATENTS
3,812,179  5/1974  Bundy .................. 260/514
3,862,984  1/1975  Pike et al. ............ 260/514

FOREIGN PATENTS OR APPLICATIONS
2,261,496  6/1973  Germany ............... 260/468

OTHER PUBLICATIONS
Corey et al., Tet. Letters, 311 (1970).

Primary Examiner—Robert Gerstl
Attorney, Agent, or Firm—Morris L. Nielsen; Robert A. Armitage

[57] ABSTRACT
This invention is a group of 8-beta, 12-alpha-PG$_2$ (prostaglandin-type) analogs having variable chain length, or methyl or phenyl substitution in the hydroxy-substituted side-chain, and processes for making them. These compounds are useful for a variety of pharmacological purposes, including anti-ulcer, inhibition of platelet aggregation, increase of nasal patency, and labor inducement at term.

5 Claims, No Drawings

$8\beta,11\beta,12\alpha$-PGF$_{2\beta}$-COMPOUNDS

CROSS REFERENCE TO RELATED APPLICATIONS

This is a division of application Ser. No. 374,405, filed June 28, 1973, which is a continuation-in-part of my copending application Ser. No. 289,317 filed Sept. 15, 1972 now abandoned.

The present invention relates to prostaglandin analogs, for which the essential material constituting a disclosure thereof is incorporated by reference here from Ser. No. 518,436, filed Oct. 29, 1974, now pending issuance as a U.S. Patent.

I claim:

1. An optically active compound of the formula

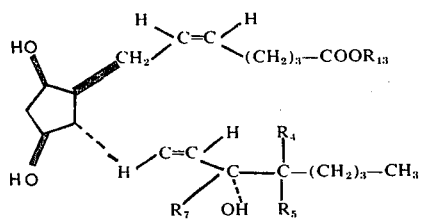

wherein $R_4$, $R_5$, and $R_7$ are hydrogen or methyl, being the same or different; with the proviso that at least one of $R_4$ and $R_5$ is methyl; and wherein $R_{13}$ is hydrogen, alkyl of one to 10 carbon atoms, inclusive, cycloalkyl of 3 to 10 carbon atoms, inclusive, aralkyl of 10 to 12 carbon atoms, inclusive, phenyl, or phenyl substituted with one, 2, or 3 chloro or alkyl of one to 4 carbon atoms, inclusive; including the lower alkanoates thereof, and the pharmacologically acceptable salts thereof when $R_{13}$ is hydrogen.

2. A compound according to claim 1, wherein $R_4$ and $R_5$ are methyl.

3. 16,16-Dimethyl-$8\beta,11\beta,12\alpha$-PGF$_{2\beta}$, a compound according to claim 2.

4. 16,16-Dimethyl-$8\beta,11\beta,12\alpha$-PGF$_{2\beta}$, methyl ester a compound according to claim 2.

5. An optically active compound of the formula

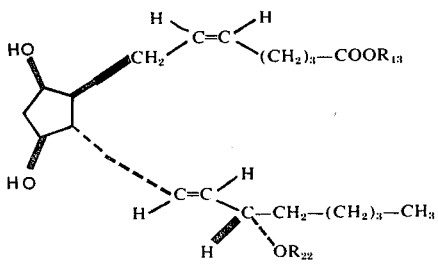

wherein $R_{13}$ is hydrogen, alkyl of one to 10 carbon atoms, inclusive, cycloalkyl of 3 to 10 carbon atoms, inclusive, aralkyl of 10 to 12 carbon atoms, inclusive, phenyl, or phenyl substituted with one, 2, or 3 chloro or alkyl of one to 4 carbon atoms, inclusive;

including the lower alkanoates thereof, and the pharmacologically acceptable salts thereof wherein $R_{13}$ is hydrogen;

wherein $R_{22}$ is alkyl of one to 4 carbon atoms, inclusive; including the lower alkanoates thereof, and the pharmacologically acceptable salts thereof wherein $R_{13}$ is hydrogen.

* * * * *

UNITED STATES PATENT OFFICE
CERTIFICATE OF CORRECTION

Patent No. 3,975,426　　　　Dated August 17, 1976

Inventor(s) Ernest W. Yankee

It is certified that error appears in the above-identified patent and that said Letters Patent are hereby corrected as shown below:

Column 1, line 23, claim 1,

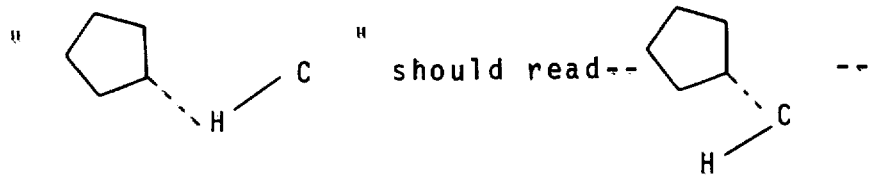

column 2, lines 16-18, claim 5,

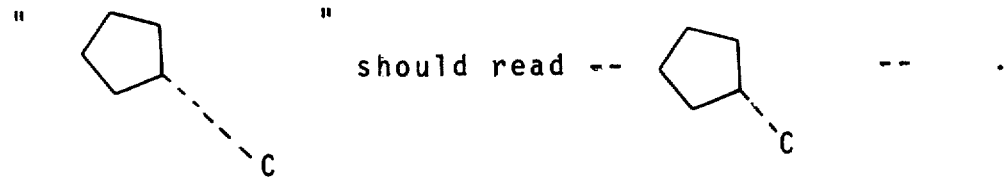

Signed and Sealed this

*Fifteenth* Day of *November 1977*

[SEAL]

Attest:

RUTH C. MASON　　　　LUTRELLE F. PARKER
*Attesting Officer*　　　*Acting Commissioner of Patents and Trademarks*